(12) United States Patent
Livak et al.

(10) Patent No.: US 9,157,116 B2
(45) Date of Patent: Oct. 13, 2015

(54) COMBINATORIAL AMPLIFICATION AND DETECTION OF NUCLEIC ACIDS

(75) Inventors: Kenneth J. Livak, San Jose, CA (US); Marc Unger, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 1171 days.

(21) Appl. No.: 12/866,018

(22) PCT Filed: Feb. 9, 2009

(86) PCT No.: PCT/US2009/033586
§ 371 (c)(1),
(2), (4) Date: Oct. 27, 2010

(87) PCT Pub. No.: WO2009/100449
PCT Pub. Date: Aug. 13, 2009

(65) Prior Publication Data
US 2011/0039725 A1    Feb. 17, 2011

Related U.S. Application Data

(60) Provisional application No. 61/027,390, filed on Feb. 8, 2008.

(51) Int. Cl.
*C12P 19/34*     (2006.01)
*C12Q 1/68*      (2006.01)

(52) U.S. Cl.
CPC ............ *C12Q 1/686* (2013.01); *C12Q 1/6834* (2013.01)

(58) Field of Classification Search
USPC ............................................... 435/6.12, 91.2
See application file for complete search history.

(56) References Cited

U.S. PATENT DOCUMENTS

| | | | |
|---|---|---|---|
| 5,723,591 A | 3/1998 | Livak et al. | |
| 6,540,895 B1 | 4/2003 | Spence et al. | |
| D488,818 S | 4/2004 | Lee et al. | |
| 6,885,982 B2 | 4/2005 | Harris et al. | |
| 6,951,632 B2 | 10/2005 | Unger et al. | |
| 7,042,649 B2 | 5/2006 | Quake et al. | |
| 7,059,348 B2 | 6/2006 | Nat | |
| 7,062,418 B2 | 6/2006 | Lee et al. | |
| 7,097,809 B2 | 8/2006 | Dam et al. | |
| 7,118,910 B2 | 10/2006 | Unger et al. | |
| 7,161,736 B2 | 1/2007 | Legrand et al. | |
| 7,192,629 B2 | 3/2007 | Lammertink et al. | |
| 7,217,367 B2 | 5/2007 | Huang et al. | |
| 7,232,109 B2 | 6/2007 | Driggs et al. | |
| 7,248,413 B2 | 7/2007 | Quake et al. | |
| 7,262,923 B2 | 8/2007 | Quake et al. | |
| 7,279,146 B2 | 10/2007 | Nassef | |
| 7,291,512 B2 | 11/2007 | Unger | |
| 7,368,163 B2 | 5/2008 | Huang et al. | |
| 7,442,556 B2 | 10/2008 | Manger et al. | |
| 7,476,363 B2 | 1/2009 | Unger et al. | |
| 7,526,741 B2 | 4/2009 | Lee et al. | |
| 7,604,965 B2 | 10/2009 | McBride et al. | |
| 7,666,361 B2 | 2/2010 | McBride et al. | |
| 7,678,547 B2 | 3/2010 | Eyal et al. | |
| 7,691,333 B2 | 4/2010 | McBride et al. | |
| 7,749,737 B2 | 7/2010 | McBride et al. | |
| 4,565,026 A1 | 8/2010 | Hansen et al. | |
| 7,792,345 B2 | 9/2010 | Taylor et al. | |
| 7,815,868 B1 | 10/2010 | Jones et al. | |
| 7,820,427 B2 | 10/2010 | Unger et al. | |
| 7,833,708 B2* | 11/2010 | Enzelberger et al. | ......... 435/6.19 |
| 7,837,946 B2 | 11/2010 | McBride et al. | |
| 8,157,434 B2* | 4/2012 | Cohen et al. | ............... 366/182.4 |
| 2002/0064779 A1 | 5/2002 | Landegren et al. | |
| 2004/0180377 A1 | 9/2004 | Manger et al. | |
| 2005/0053952 A1 | 3/2005 | Hong et al. | |
| 2005/0089889 A1 | 4/2005 | Ramsing et al. | |
| 2005/0233363 A1 | 10/2005 | Harding et al. | |
| 2005/0252773 A1* | 11/2005 | McBride et al. | ............. 204/450 |
| 2005/0260640 A1 | 11/2005 | Andersen et al. | |
| 2006/0172408 A1 | 8/2006 | Quake et al. | |
| 2006/0281183 A1 | 12/2006 | Sun et al. | |
| 2007/0065847 A1 | 3/2007 | Namsaraev et al. | |
| 2007/0134807 A1 | 6/2007 | Bao et al. | |
| 2007/0224617 A1 | 9/2007 | Quake et al. | |
| 2007/0248971 A1 | 10/2007 | Maerkl et al. | |
| 2008/0050283 A1 | 2/2008 | Chou et al. | |
| 2008/0075380 A1 | 3/2008 | Dube et al. | |
| 2008/0108063 A1 | 5/2008 | Lucero et al. | |

(Continued)

FOREIGN PATENT DOCUMENTS

WO        2005/107938 A2    11/2005
WO    WO 2009/100449 A1    8/2009

OTHER PUBLICATIONS

International Search Report for PCT/US2009/033586 mailed May 12, 2009, 2 pages.
Baner et al., "Parallel Gene Analysis With Allele-Specific Padlock Probes and Tag Microarrays", Nucleic Acids Research, vol. 31, No. 17 e103, pp. 1-7, (2003).
Cao, Review, "Recent Developments in Ligase-Mediated Amplification.And Detection", TRENDS in Biotechnology, vol. 22, No. 1, pp. 38-44, (Jan. 2004).
Gullberg et al., Cytokine Detection by Antibody-Based Proximity Ligation, *Proc Natl. Acad Sci USA*, 101(22):8420-8440 (2004).
Fredriksson et al., "Protein Detection Using Proximity-Dependent DNA Ligation Assays," *Nat Biotechnol.*, 20:473-477 (2002).
Heid et al., "Real Time Quantitative PCR," Genome Res., 6:986-994.
Landegren et al., Padlock and Proximity Probes for in Situ and Array-Based Analyses: Tools for the Post-genomic Era, *Comparative and Functional Genomics*, 4:525-530 (2003).

(Continued)

*Primary Examiner* — Kenneth Horlick
(74) *Attorney, Agent, or Firm* — Kilpatrick Townsend & Stockton LLP (57) ABSTRACT

High throughput methods are used that combine the features of using a matrix-type microfluidic device, labeled nucleic acid probes, and homogenous assays to detect and/or quantify nucleic acid analytes. The high throughput methods are capable of detecting nucleic acid analyes with high PCR and probe specificity, producing a low fluorescence background and therefore, a high signal to noise ratio. Additionally, the high throughput methods are capable of detecting low copy number nucleic acid analyte per cell.

16 Claims, 7 Drawing Sheets

(56) References Cited

U.S. PATENT DOCUMENTS

| | | |
|---|---|---|
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde et al. |
| 2009/0035838 A1 | 2/2009 | Quake et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0239308 A1 | 9/2009 | Dube et al. |
| 2009/0291435 A1 | 11/2009 | Unger et al. |
| 2009/0317798 A1 | 12/2009 | Heid et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2014/0357513 A1 | 12/2014 | Lucero et al. |

OTHER PUBLICATIONS

Landegren et al., "Molecular Tools for a Molecular Medicine: Analyzing Genes, Transcripts, Proteins Using Padlock and Proximity Probes," *J Mol Recognit.*, 7:194-197 (2004).

Ng et al., Review, Components for integrated Poly(dimethylsiloxane) Microfluidic Systems, Electrophoresis, 23, pp. 3461-3473 (2002).

Nilsson et al., Analyzing Genes Using Closing and Replicating Circles, *Trends Biotechnol.*, 24:83-88 (2006).

Nilsson et al., Padlock Probes: Circularizing Oligonucleotides for Localizing DNA Detection, *Science*, 265:2085-2088 (1994).

Roth et al., Expression Profiling Using a Hexamer-Based Universal Microarray, vol. 22, No. 4,, Nature Biotechnology, pp. 418-426 (Apr. 2004).

Supplemental Table 3, ROTH et al., Expression Profiling Using a Hexamer-Based Universal Microarray, vol. 22, No. 4, Nature Biotechnology, two pages, (Apr. 2004).

Szemes et al., Diagnostic Application of Padlock Probes—Multiplex Detection of Plant Pathogens Using Universal Microarrays, *Nucleic Acids Res.*, 33(8):e70, 13 pages, (2005).

Roche Diagnostics GmbH, "RealTime ready, Universal ProbeLibrary, Redefining and revolutionizing real-time qPCR assays," brochure, 32 pages, (2009).

\* cited by examiner

FIGURE 1

| P40 | P72 | P103 | P120 | P161 | P14 | P159 | P68 | P78 | P71 |
|---|---|---|---|---|---|---|---|---|---|
| CD58 | IL8 | TMSL8 | DEFB125 | S100A12 | DLEU1 | NDUFAB1 | MOSPD1 | S100A8 | CCL20 |
| SOD1 | FABP1 | GZMA | B2M | POLR1D | SCGB2A2 | TMEM5 | TMEM111 | HGD | LRRC17 |
| MIF | FGF22 | CKAP2 | LMBRD1 | IL1F6 | CGA | ARMET | TMEM93 | CRISP3 | POLI |
| RAB11A | FABP4 | HB-1 | INSL4 | PIGB | POLB | BEX1 | FLJ37549 | HOXA5 | GNG13 |
| HBZ | CD55 | ADI1 | EYA3 | COX7A1 | MYLPF | HIGD1B | DNAJB9 | TNNI2 | POLR2G |
| PGLYRP1 | RRAGB | ADM | PBK | HIP2 | ELSPBP1 | C12orf24 | PPP6C | NAP1L3 | BRS3 |
| MMP7 | BIRC2 | MDS1 | FBXO22 | EDN1 | ARHGDIB | ATG3 | CSNK2A2 | TESC | ZNF101 |
| FOXB1 | CHCHD2 | GABRA6 | DUSP21 | ASB4 | CDX4 | NAT2 | KNTC2 | ANXA13 | GSTT1 |
| DCXR | NPC2 | OMG | COMMD3 | PURG | PEX13 | DLG7 | ESX1 | DCT | RRH |
| GGH | PRPSAP1 | CEP55 | GPR22 | C6orf78 | SERPINI1 | CD3D | NELL1 | CCNB2 | MS4A4A |
| KYNU | MAB21L1 | CENPA | PPP1CC | SNX4 | ABHD10 | OR1F1 | MTRF1 | SLC30A6 | SFRS10 |
| PCNA | NEDD8 | SMAP | FPGT | LEPROTL1 | TMSB4Y | ASNSD1 | C4BPB | HADH2 | PITX1 |
| S100A5 | S100P | UGT2A3 | CRYGB | GUF1 | HDHD1A | MEPE | HOXB7 | KCNE1L | GFPT1 |
| IL6 | SNRPD3 | ACADM | SERPINB2 | GUCA2B | PPARG | CCR3 | MMD | HOXA7 | THRSP |
| MGMT | MDS032 | C17orf40 | DHDH | ZNF557 | RAB32 | GIF | ASRGL1 | NOL4 | MMP13 |
| HIST1H1D | LDHA | NRGN | FLJ20130 | GZMM | ELAVL4 | NPBWR2 | CD3E | HSD17B2 | PIK3C3 |
| TYR | CPB1 | ZMYM1 | WDR71 | ITGB1BP2 | SGCE | RAB30 | HTR5A | EIF2AK2 | C10orf93 |
| ACAT1 | PMP2 | C14orf122 | RARRES3 | CYP3A5 | MELK | MFSD1 | WNT2B | FXYD7 | IL13 |
| GULP1 | SLC25A4 | NUDT11 | C9orf30 | FBXO39 | LHX5 | SPOCK3 | MASP2 | PSMC4 | LUM |
| ATOH1 | MMP21 | SLC17A2 | CDK4 | AHSG | BPHL | ACTL6B | JUNB | RHAG | GAS1 |
| TNNC2 | CUEDC2 | SCAP1 | SERGEF | CD180 | CHEK1 | C9orf121 | C16orf3 | HOXB8 | GAPDHS |
| C17orf69 | SEMA3A | ANXA5 | CDK5 | RPL3L | AMBP | FGB | PLA2G2A | TRIM36 | GSTP1 |
| ARF5 | CCDC15 | STAT4 | UGCG | ADCYAP1 | C16orf33 | NR1I3 | MDM2 | FLI1 | RNUT1 |
| C16orf24 | NEIL3 | SOX15 | SCO2 | TRPC1 | ZNF140 | CASP5 | KCNJ3 | KCNE4 | DHX15 |

|  | R1,R5,R9,R13 | R2,R6,R10,R14 | R3,R7,R11,R15 | R4,R8,R12,R16 |
|---|---|---|---|---|
|  | P1 | P2 | P3 | P4 |
| F1,F2,F3,F4 |  |  |  |  |
| F5,F6,F7,F8 |  |  |  |  |
| F9,F10,F11,F12 |  |  |  |  |
| F13,F14,F15,F16 |  |  |  |  |

FIGURE 4

|  | R1,R5,R9,R13<br>P1 | R2,R6,R10,R14<br>P2 | R3,R7,R11,R15<br>P3 | R4,R8,R12,R16<br>P4 |
|---|---|---|---|---|
| F1,F2,F3,F4 | F1,F2,F3,F4<br>R1,R5,R9,R13<br>P1 | F1,F2,F3,F4<br>R2,R6,R10,R14<br>P2 | F1,F2,F3,F4<br>R3,R7,R11,R15<br>P3 | F1,F2,F3,F4<br>R4,R8,R12,R16<br>P4 |
| F5,F6,F7,F8 | F5,F6,F7,F8<br>R1,R5,R9,R13<br>P1 | F5,F6,F7,F8<br>R2,R6,R10,R14<br>P2 | F5,F6,F7,F8<br>R3,R7,R11,R15<br>P3 | F5,F6,F7,F8<br>R4,R8,R12,R16<br>P4 |
| F9,F10,F11,F12 | F9,F10,F11,F12<br>R1,R5,R9,R13<br>P1 | F9,F10,F11,F12<br>R2,R6,R10,R14<br>P2 | F9,F10,F11,F12<br>R3,R7,R11,R15<br>P3 | F9,F10,F11,F12<br>R4,R8,R12,R16<br>P4 |
| F13,F14,F15,F16 | F13,F14,F15,F16<br>R1,R5,R9,R13<br>P1 | F13,F14,F15,F16<br>R2,R6,R10,R14<br>P2 | F13,F14,F15,F16<br>R3,R7,R11,R15<br>P3 | F13,F14,F15,F16<br>R4,R8,R12,R16<br>P4 |

|  | P66 | P17 | P01 | P03 | P10 | P25 | P36 | P63 |
|---|---|---|---|---|---|---|---|---|
|  | R1…R57 | R2…R58 | R3…R59 | R4…R60 | R5…R61 | R6…R62 | R7…R63 | R8…R64 |
| F1-8 | 1.DRD4 | 2.RPL32 | 3.CSF2 | 4.TFRC | 5.USP11 | 6.NDUFV2 | 7.ENSA | 8.ACTB |
| F9-16 | 9.IL1A | 10.PROC | 11.CSNK2B | 12.PHB2 | 13.TUFM | 14.FN1 | 15.P4HB | 16.RPN2 |
| F17-24 | 17.CD19 | 18.HMOX1 | 19.LIG1 | 20.ICAM1 | 21.ANXA2 | 22.TIMP1 | 23.SLC25A3 | 24.PSAP |
| F25-32 | 25.POLR2L | 26.PGK1 | 27.HSPD1 | 28.NCF1 | 29.PREP | 30.GAPDH | 31.ILF2 | 32.VIM |
| F33-40 | 33.CTLA4 | 34.EEF1G | 35.COX4I1 | 36.ARHGDIA | 37.SNRPB | 38.HSP90AA | 39.TP53 | 40.KRT18 |
| F41-48 | 41.PABPC1 | 42.CANX | 43.PSMB10 | 44.CD81 | 45.SPARC | 46.NEDD8 | 47.CAP1 | 48.NONO |
| F49-56 | 49.TGFB1 | 50.CCND1 | 51.ATP6AP1 | 52.GDF11 | 53.PPIB | 54.EEF2 | 55.GPI | 56.SQSTM1 |
| F57-64 | 57.SEP2 | 58.CTNNB1 | 59.CCT3 | 60.GZMB | 61.CDC20 | 62.CA9 | 63.CPNE1 | 64.ALDOA |

FIGURE 7

COMBINATORIAL AMPLIFICATION AND DETECTION OF NUCLEIC ACIDS

CROSS-REFERENCE TO RELATED APPLICATIONS

This application claims priority to and benefit under 35 U.S.C. §119(e) to provisional application Ser. No. 61/027,390, filed Feb. 8, 2008, the disclosure of which is herein expressly incorporated by reference in its entirety.

BACKGROUND OF THE INVENTION

1. Field of the Invention

The invention is generally related to high throughput methods and strategies to detect and/or quantify nucleic acid analytes employing matrix-type microfluidic devices. In particular, the invention uses high throughput homogeneous methods to detect and/or quantify nucleic acid analytes having the desired features of high specificity and a high signal to noise ratio.

2. Related Art

The ability to detect specific nucleic acid sequences in a sample has resulted in new approaches in diagnostic and predictive medicine, environmental, food and agricultural monitoring, molecular biology research, and many other fields. High-throughput detection of specified epitopes, nucleic acids, proteins, and protein complexes promises to have a similar impact.

Various methods for such analysis have been developed, including multiplexing methods that allow simultaneous detection of large numbers of targets. Additional methods, especially methods that allow detection of many targets across a broad range of concentrations in a sample would be of great benefit.

BRIEF SUMMARY OF THE INVENTION

The invention provides methods that may combine the features of using a high throughput microfluidic device, labeled nucleic acid probes, and homogenous assays to detect and/or quantify nucleic acid analytes with high PCR and probe specificity, low fluorescence background and thus a high signal to noise ratio. Additionally, the methods of the invention may be used to detect and/or quantify low copy number nucleic acid analyte per cell.

According to one aspect of the invention, a method for the detection of a plurality or nucleic acid analytes may combining aliquots of nucleic acid containing sample with labeled nucleic acid probes and PCR primers in separate compartments of a microfluidic device and segregating the aliquots from each other, performing a homogeneous assay, and querying each of the samples for the presence of a target nucleic acid analyte. The nucleic acid containing sample may be a cDNA containing sample.

Moreover, the combining step may include introducing into each column a column solution, where at least two columns do not receive the same column solution, and where each column solution comprises a unique plurality of reverse primers and one or more probes; introducing into each row a row solution, where at least two rows do not receive the same row solution and where each row solution comprises a unique plurality of forward primers. In each compartment, combining a column solution and a row solution where the primers in each column solution and the primers in each row solution are selected to provide a plurality of forward-reverse primer combinations. Each combination of forward-reverse primers may be capable of amplifying a unique region of said nucleic acid to produce a plurality of amplicons and the probe(s) in each column solution may include a sequence that specifically bind to one or more of the amplicons, and in aggregate the probe(s) in each column solution bind each amplicon.

The assay method may further include performing a preliminary amplification reaction on the nucleic acid sample to generate a pre-amplified sample. The preliminary amplification reaction may include making a reaction mix containing the nucleic acid containing sample, the forward primers, and the reverse primers, and then subjecting the reaction mix to PCR amplification. The reaction mix may be subjected in a range of about 10 cycles to about 18 cycles of PCR amplification. In particular, the reaction mix may be subjected to about 14 cycles of PCR amplification.

The homogenous assay may be conducted under conditions which may promote the hybridization of the probe to the target nucleic acid analyte. Moreover, the homogenous assay may be conducted under conditions which promotes the amplification of target nucleic acid analyte. The homogenous assay may include performing a PCR, such as real time PCR.

The nucleic acid probe may be capable of detecting about 8-mer and/or 9-mer motifs on the target nucleic acid analyte. The nucleic acid probe may be labeled on a 5'-end with a fluorescent molecule, such as fluorescein, and labeled on a 3' end with a dark quencher dye. The 8-mer or 9-mer motifs on the target nucleic acid analyte may be ranked on one side by the forward primer and on the other side by the reverse primer.

The microfluidic device may be a 48×48 array of reaction chambers. The microfluidic array may be a 96×96 array of reaction chambers. At least about 1000 target nucleic acid analytes may be detected using the microfluidic devices of the invention.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

FIG. 2 is a probe/amplicon association matrix.

DETAILED DESCRIPTION OF THE INVENTION

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

PNA is peptide nucleic acid
LNA is locked nucleic acid
DA is dynamic array
PCR is polymerase chain reaction
FRET is fluorescence resonance energy transfer
PLP is padlock probe The term "about," as used herein, is used to describe a range of values, applies to both the upper limit and lower limit of the range. For example, the phrase "ranges from about 10 to 100" has the same meaning as "ranges from about 10 to about 100." Moreover, when referring to amount, the term "about" generally means+/−10%. For example, the phrase "about 5 µm" means 5 µm+/−10%.

The term "adjacent" as used herein, generally refers to the positioning of the primer with respect to the probe on its complementary strand of the target nucleic acid analyte. The primer and probe may be separated in a range of about 1 to about 20 nucleotides, more specifically, in a range of about 1 to about 10 nucleotides, or may directly abut one another.

The term "analyte" as used herein, generally refers to a nucleic acid molecule or mixture of nucleic acid molecules, defined infra, that is to be detected or quantified using the methods of the invention. The terms "target nucleic acid analyte" and "nucleic acid analyte" are used interchangeably with the term "analyte" for the purposes of this invention.

The terms "complementary" or "complementarity" as used herein, may include the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

The term "covalently attached" as used herein, generally refers to an attachment of one molecular moiety to another molecular moiety through covalent chemical bonds.

The term "dye" as used herein, generally refers to any organic or inorganic molecule that absorbs electromagnetic radiation at a wavelength greater than or equal 340 nm.

The term "fluorescent dye" as used herein, generally refers to any dye that emits electromagnetic radiation of longer wavelength by a fluorescent mechanism upon irradiation by a source of electromagnetic radiation, such as a lamp, a photodiode, or a laser.

The term "homogenous assay" as used herein, generally refers to a method to detect or quantify a nucleic acid analyte that requires no post-assay processing to record the result of the assay. The homogenous assays may be carried out in closed tubes or microfluidic arrays where no further addition of reagents or supplementary chemicals are necessary to record the result once the assay is started. Homogenous assays allow recordation of the result of the assay in real time, meaning that the result of the assay can be continuously recorded as the assay progresses in time.

The term "hydrolysis probes" as used herein are generally described in U.S. Pat. No. 5,210,015 incorporated herein by reference in its entirety. Hydrolysis probes take advantage of the 5'-nuclease activity present in the thermostable Taq polymerase enzyme used in the PCR reaction (TaqMan® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe may anneal downstream of one of the primers that defines one end of the amplification target site on the nucleic acid target analyte in the PCR reaction. Using the polymerase activity of the Taq enzyme, amplification of the target nucleic acid analyte is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, the hydrolysis probes of the invention may capable of detecting 8-mer or 9-mer motifs that are common in the human and other transcriptomes and may have a high $T_m$ of about 70° C. enabled by LNA analogs.

The term "label" as used herein refers to any atom or molecule which can be used to provide a detectable and/or quantifiable signal. In particular, the label can be attached to a nucleic acid or protein. Labels may provide signals detectable by fluorescence, radioactivity, colorimetric, X-ray diffraction or absorption, magnetism, enzymatic activity, and the like.

The term "nucleic acid" as used herein generally refers to cDNA, DNA, RNA, single-stranded or double-stranded and any chemical modification thereof, such as PNA and LNA. LNAs are described in U.S. Pat. Nos. 6,794,499, 6,670,461, 6,262,490, and 6,770,748 herein incorporated by reference in their entirety. Nucleic acids may be of any size. Nucleic acid modifications may include addition of chemical groups that incorporate additional charge, polarizability, hydrogen bonding, electrostatic interaction, and functionality to the individual nucleic acid bases or to the nucleic acid as a whole. Such modifications may include modified bases such as 2'-position sugar modifications, 5-position pyrimidine modifications, 8-position purine modifications, modifications at cytosine exocylcic amines, substitutions of 5-bromo-uracil, backbone modifications, methylations, unusual base pairing combinations such as the isobases isocytidine and isoguanidine and the like. The nucleic acid can be derived from a completely chemical synthesis process, such as a solid phase mediated chemical synthesis, or from a biological origin, such as through isolation from almost any species that can provide nucleic acid, or from processes that involve the manipulation of nucleic acids by molecular biology tools, such as DNA replication, PCR amplification, reverse transcription, or from a combination of those processes.

The term "nucleic acid probe" as used herein is a nucleic acid that carriers at least one covalently attached dye, such as a fluorescent dye. In particular, the probe does not contain a sequence complementary to sequences used to prime the PCR reaction.

The term "padlock probe" or "PLP" as used herein, generally refers to linear oligonucleotides having a length of about 100 base pairs. The sequences at the 3' and 5' ends of the PLP are complementary to adjacent sequences in the target nucleic acid analyte. In the central, noncomplementary region of the PLP there is a "tag sequence" that may be used to identify the specific PLP. The tag sequence may be flanked by universal primer sites or unique and/or specific primer sites, which allow PCR amplification of the tag sequence. Upon hybridization to the target, the 5' and 3' ends of the PLP are brought into close proximity and may be subsequently ligated. The resulting product is a circular probe molecule catenated to the target nucleic acid analyte. The tag regions of circularized PLPs may be amplified and quantified and/or detected using TAQMAN® Real Time PCR, for example. The presence and amount of amplicon may be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8. The above references are incorporated by reference herein in their entirety.

The phase "preliminary amplification reaction" as used herein, generally refers to processes for preparing the sample prior to running the homogenous assay. The term "pre-amplified sample" may be used interchangeably with the phrase "preliminary amplification reaction" for the purposes of the invention herein.

The term "purification," as used herein, generally refers to any process by which proteins, polypeptides, or nucleic acids are separated from other elements or compounds on the basis of charge, molecular size, or binding affinity.

The term "quencher" as used herein, generally refers to dye that reduces the emission of fluorescence of another dye.

The term "querying" as used herein, generally refers to determining whether a target-specific probe is associated with (e.g., bound to or cantenated with) the nucleic acid analyte, and optionally quantifying the amount of target-specific probe in the sample.

A "sample" as used herein, generally refers to a sample of tissue or fluid from a human or animal including, but not limited to plasma, serum, spinal fluid, lymph fluid, the external sections of the skin, respiratory, intestinal and genitourinary tracts, tears, saliva, blood cells, tumors, organs, tissue and sample of in vitro cell culture constituents. In particular, the sample may be single cells, paraffin embedded tissue samples, and needle biopsies. Moreover, a sample may include environmental samples such as lake water, and food samples.

The phrase "substantially purified," or "substantially isolated," as used herein generally includes nucleic or amino acid sequences that are removed from their natural environment, isolated or separated, and are at least about 60% free, specifically at least about 75% free, and most specifically at least about 90% free from other components with which they may be associated with, and includes recombinant or cloned nucleic acid isolates and chemically synthesized analogs or analogs biologically synthesized by systems.

The invention relates generally to methods and products for use in the field of molecular biology and high throughput analysis using a matrix-type microfluidic device. In particular, the invention provides methods for detecting nucleic acid analytes through their interactions with a nucleic acid probe, such as a hydrolysis probe, a hairpin probe, a padlock probe (PLP) or a hybridization probe. The methods of the invention combine the features of using a high throughput microfluidic device, labeled nucleic acid probes, and homogenous assays to detect and/or quantify nucleic acid analytes with high PCR and probe specificity, allow detection of low copy number nucleic acid analyte per cell, have low fluorescence background and thus have a high signal to noise ratio. The homogeneous assays of the invention may have a dynamic range of at least about 3 orders of magnitude, more often at least about 4, even more often at least about 5, even more often at least about 6, often at least about 7, and sometimes at least about 8 orders of magnitude.

The microfluidic device suitable for use with the methods of the invention may be a matrix-type microfluidic device. The matrix-type device may allow the simultaneous pair-wise combination of a plurality of substrate/reagent pairs in separate isolated reaction chambers such as the simultaneous pair-wise combination of a plurality of targets and probes. The device may be configured to contain a different combination of probes and targets in each of the different chambers. The number of separate reaction chambers may be greater than about 50, greater than about 100, more often greater than about 500, even more often greater than about 1000, and sometimes greater than about 5000, or greater than about 10,000.

The matrix-type microfluidic device may be a Dynamic Array microfluidic device ("DA"), which may be a matrix-type microfluidic device, designed to isolate pair-wise combinations of nucleic acid analytes and reagents (e.g., amplification primers, detection probes, PCR primers, etc.), and suited for carrying out qualitative and quantitative homogeneous assays such as real-time quantitative PCR analysis. The DA microfluidic device may be fabricated, at least in part, from an elastomer. Dynamic Arrays are described in PCT publication WO05107938A2 (Thermal Reaction Device and Method For Using The Same) and US Pat. Publication US20050252773A1, both expressly incorporated by reference in their entirety. In one embodiment a microfluidic device described in U.S. patent application Ser. No. 12/018, 138 (U.S. Patent Publication No. 20080223721) "High Efficiency and High Precision Microfluidic Devices and Methods," incorporated herein by reference for all purposes, is used. Fabrication methods using elastomeric materials and methods for design of devices and their components have been described in detail in the scientific and patent literature. See, e.g., Unger et al., 2000, Science 288:113-16; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767, 706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application publication Nos. 2004/0115838, 20050072946; 20050000900; 20020127736; 20020109114; 20040115838; 20030138829; 20020164816; 20020127736; and 20020109114; PCT patent publications WO 2005/084191; WO05030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23," Hong et al, 2004, "A nanoliter-scale nucleic acid processor with parallel architecture" Nature Biotechnology 22:435-39.

U.S. Patent Publication No. 20080223721 describes a matrix-type device that can be used to practice the invention. Additionally, FIG. 21 of WO05107938A2 also describes an exemplary matrix design having a first elastomeric layer 2110 (1st layer) and a second elastomeric layer 2120 (2d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet, containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO05107938A2) that the DA may be used for reacting M number of different samples with N number of different reagents. Although the DA described above in WO05107938 are well suited for conducting the assays of the invention, the invention is not limited to any particular device or design. Any device that partitions a sample, and allows independent pair-wise combinations of reagents and sample may be used.

The homogeneous assays of the invention may be carried out using microfluidic devices of various configurations. For example, one sample may be simultaneously assayed for 2304 nucleic acid analytes using a Dynamic Array microfluidic device with a 48×48 array of reaction chambers. It will be understood that other configurations are possible and contemplated such as, for example, 48×96; 96×96; 30×120; etc. Table 1 below illustrates the possible number of assays that may be run per sample number using a 48×48 array and a 96×96 array of reaction chambers.

TABLE 1

| Number of Samples Analyzed | Number of Assays on a 48 × 48 array | Number of Assays on a 96 × 96 array |
| --- | --- | --- |
| 1 | 2304 | 9216 |
| 2 | 1152 | 4608 |
| 3 | 768 | 3072 |
| 4 | 576 | 2304 |
| 6 | 384 | 1536 |
| 8 | 288 | 1152 |
| 12 | 192 | 768 |
| 16 | 144 | 576 |
| 24 | 96 | 384 |
| 32 | — | 288 |
| 48 | — | 192 |

According to an embodiment of the invention, the detection and/or quantification of a plurality of nucleic acid analytes from a sample may generally be carried out by obtaining a sample, optionally pre-amplifying the sample, aliquoting the sample and distributing the pre-amplified sample into reaction chambers of a microfluidic device containing the appropriate buffers, primers, probes and enzymes, performing a homogenous assay for the target nucleic analytes of interest, and querying the aliquots for the presence of nucleic acid analytes.

Figure 1:
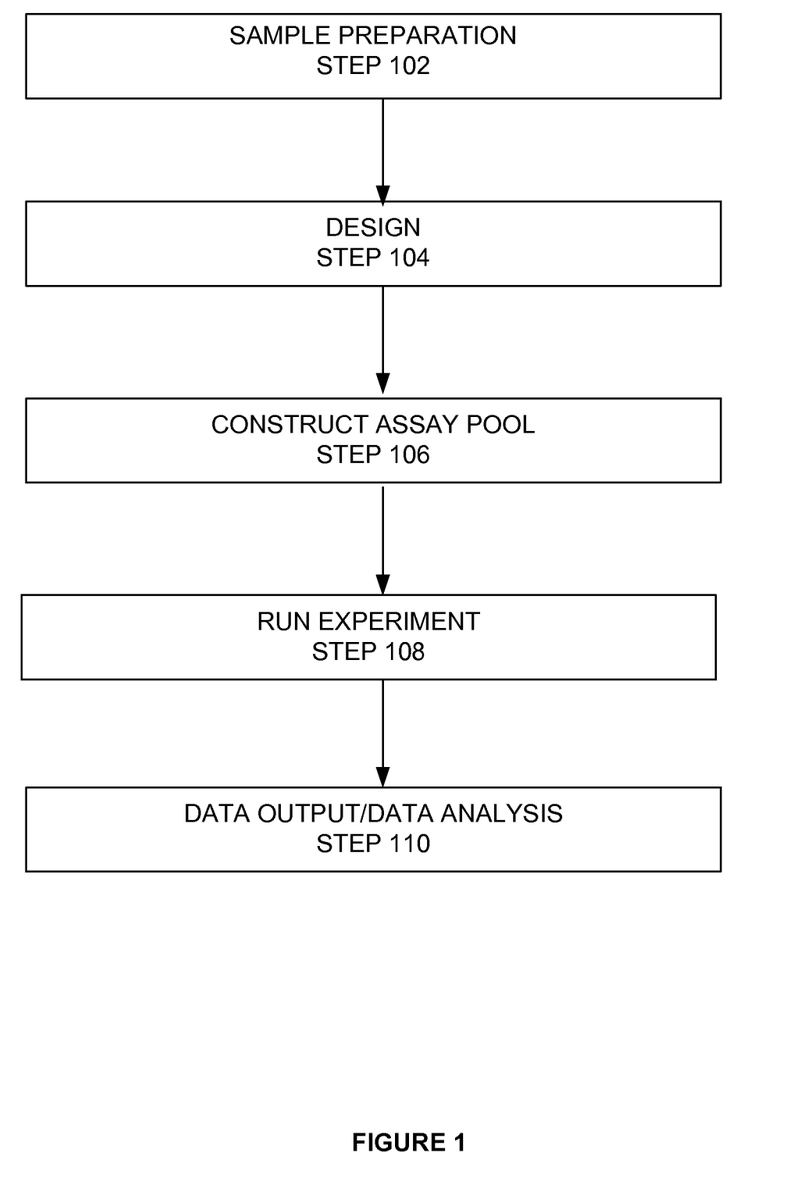
FIG. 1 is a flow chart illustrating a method for using a dynamic array to survey a large number of genes.

FIG. 1 is a flow chat illustrating a method for using a dynamic array to survey a large number of genes according to principles of the invention. This figure is provided for illustration and is not intended to limit the invention or imply a specific order of steps. As one skilled in the art would appreciate, the order of the steps designated within the flow chart may be varied. In step 102, a sample is obtained from a subject containing the suspected nucleic acid sequence(s) of interest. In step 104, the probes and primers are determined for screening the genes of interest. In step 106, the assay pools are constructed, i.e., the primers and probes are pooled in the appropriate configurations. In step 108, the PCR experiment is run. In step 110, the data is displayed and analyzed. These steps are described in detail below.

Sample Preparation

In step 102, according to one embodiment of the invention, a sample is obtained which is suspected of containing the target nucleic acid analyte of interest (i.e., the amplicon). The nucleic acid of interest may be isolated using methods well known in the art, with the choice of a specific method depending on the source, nature of nucleic acid, and similar factors. After the nucleic acid sample has been isolated from the sample, the sample may be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example.

Molecular Probe and Primer Identification

In step 104, the appropriate molecular probes to be used in the real-time PCR reaction are identified. The molecular probes may be hydrolysis probes capable of detecting 8-mer and 9-mer motifs that are common in a transcriptome, such as a human transcriptome. Specifically, the hydrolysis probes may have a high $T_m$, which is enabled by the presence of LNA analogs in the probe sequence. The hydrolysis probes, as described above, are labeled at their 5' end with a fluorescent molecule such as fluorescein and a dark quencher dye at their 3' end. The probes may be applied as a single probe per assay and should be easily adopted in homogenous assays, in particular PCR based assays and provide the results in real time. The molecular probes may be obtained from any commercially available source, such as the Universal Probe Library (UPL) (Roche Applied Sciences, Indianapolis, Ind.).

In one aspect of the invention, the UPL probe sequences are identified within the amplicon sequences (the amplicon sequences may be obtained from Genbank, for example) and an association matrix may be generated to indicate which amplicons are associated with specific UPL probe sequences. FIG. 2 is an example of a probe/amplicon association matrix showing 10 UPL probes with 24 amplicons associated with each probe. In FIG. 2, the different UPL probes are listed across the top row and the amplicons associated with the UPL probe are listed in the column below. A design software may be implemented to identify UPL probe sequences within the amplicon and arrange the amplicons that are associated with the same probe in an matrix output.

In step 104, the PCR primers are also determined. The PCR primers must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art appreciates how to select appropriate PCR primer pairs to amplify the target nucleic acid analyte of interest.

Figure 3:
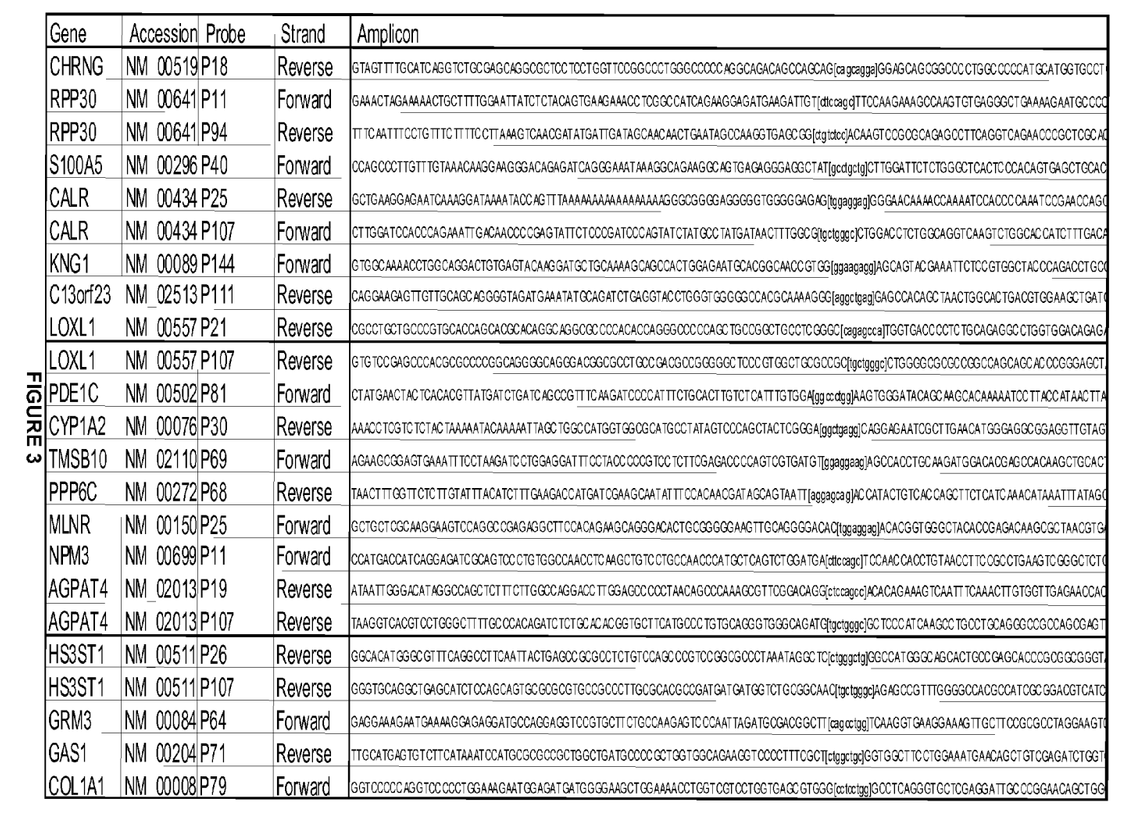
FIG. 3 is a gene/probe/amplicon association table.

For example, the PCR primers may be designed by using any commercially available software or open source software, such as Primer3 or by accessing the Roche UPL website. The amplicon sequences are inputted into the Primer3 program with the UPL probe sequences in brackets to ensure that the Primer3 program will design primers on either side of the bracketed probe sequence. FIG. 3 is a matrix showing the target gene name, the accession number, the specific UPL probe, and the amplicon sequence. Within the amplicon sequence, the probe sequence is contained between the brackets.

Molecular Probe and Primer Pool Configuration

In step 106, the assay pools are constructed, i.e., the primers and probes are pooled in the appropriate configurations. In one aspect of the invention, prior to pooling, the PCR primers may be purified by using a Sephadex column (Amersham Biosciences, Inc., Piscataway, N.J.) or other methods known by those skilled in the art. Primer purification may improve the sensitivity of the dynamic array assay.

Figure 4:
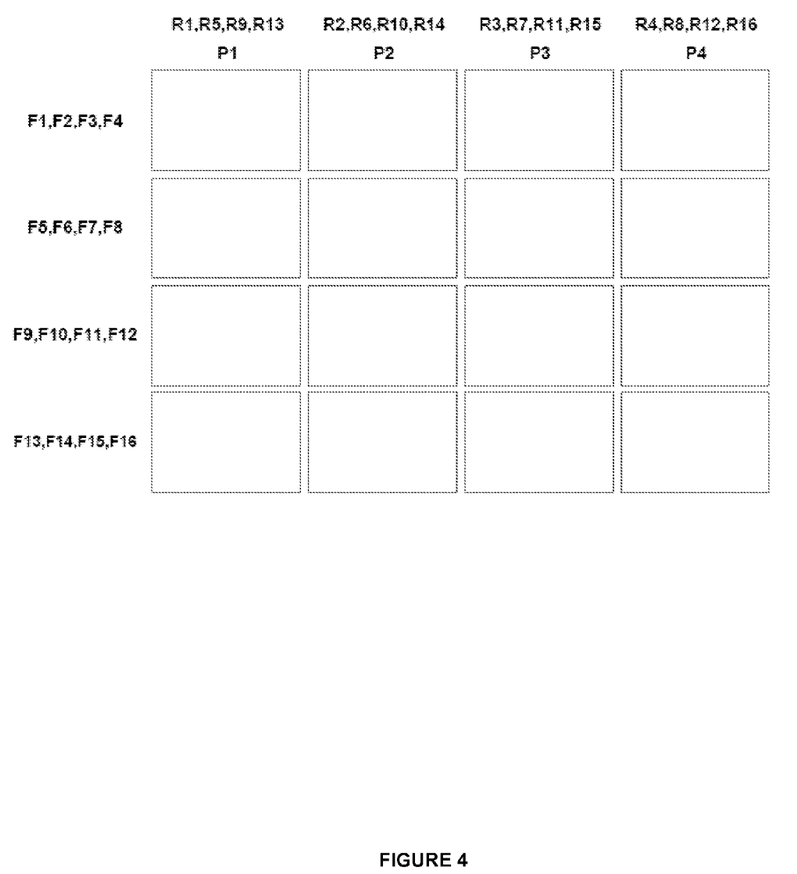
FIG. 4 is a schematic illustrating the combinational mixing of forward and reverse primers in order to generate functional PCR assays on a 4×4 device according to principles of the invention.
Figure 5:
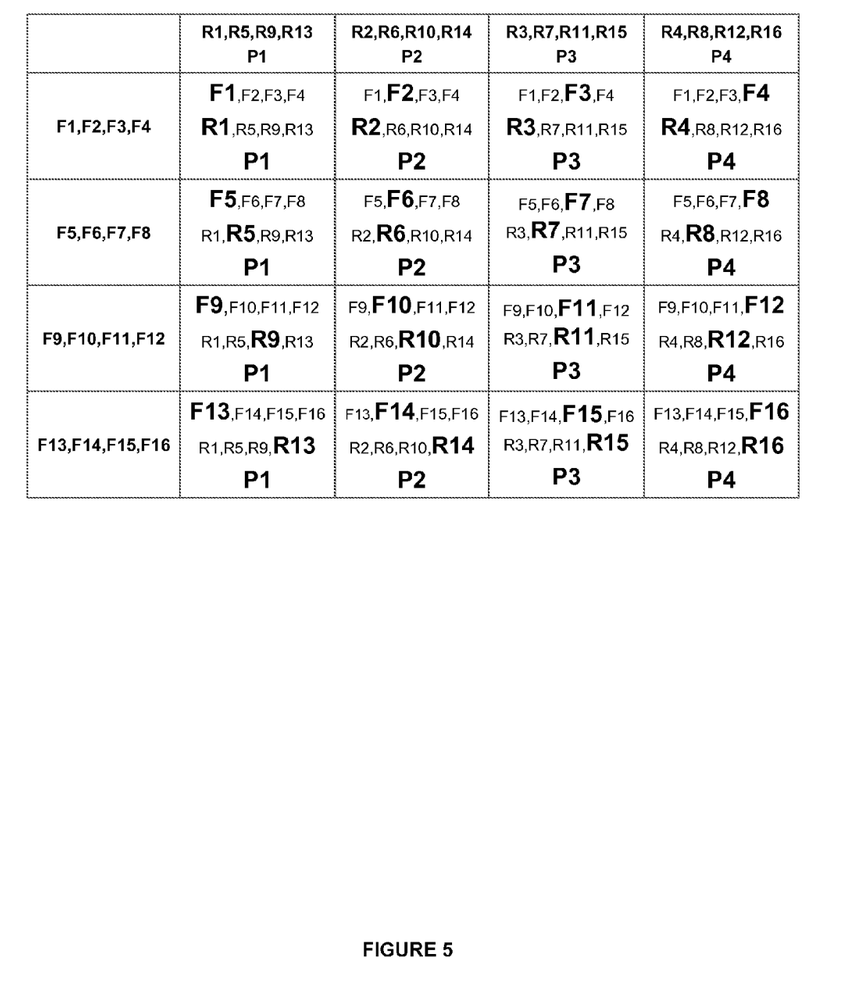
FIG. 5 is a schematic illustrating the 4×4 device of FIG. 1 after the rows and columns have been filled according to principles of the invention.

FIG. 4 illustrates the combinational mixing of forward and reverse primers with sample in order to generate functional PCR assays on a 4×4 device. In FIG. 1, a solution containing forward primers F1, F2, F3, and F4 and the sample is going to fill the 4 chambers in the first row of the device. A solution containing reverse primers R1, R5, R9, R13 and probe P1 is going to fill the 4 chambers in the 1st column of the device. The other rows and columns will be filled as shown in FIG. 1. FIG. 5 illustrates the 4×4 device after the rows and columns have been filled. Each chamber contains sample, 4 forward primers, 4 reverse primers, and 1 probe. As illustrated in FIG. 5, only 1 forward primer and 1 reverse primer will generate a PCR product. Therefore, only one distinct PCR product is generated in each of the 16 chambers of the device. The combinational mixing scheme described above is exemplary and not intended to be limiting, and one skilled in the art would appreciate that different combinational mixing schemes are also possible that may be used with the homogeneous assays of the invention. Furthermore, for simplicity, the combinational mixing scheme above was illustrated using a 4×4 array. One skilled in the art appreciates that the combinational mixing scheme may be scaled-up appropriately depending upon the number of reaction chambers present on the microfluidic device. For example, it is appreciated that a solution may contain up to about 1, 4, 10, 15, 20, 25, 30, 35, 40, 45, 50, 55, 60, 65, 70, 75, 80, 90, and 100 different forward primers and a solution may contain up to about 1, 4, 10, 15, 20, 25, 30, 35, 40, 45, 50, 55, 60, 65, 70, 75, 80, 90, and 100 different reverse primers depending upon the number of reaction chambers present in the microfluidic device.

Aliquots of the sample and forward primers are distributed into separated compartments of a microfluidic device and combined with the appropriate reagents. In particular, the aliquot may have a volume of in the range of about 1 picoliter to about 500 nanoliters, more often in the range of about 100 picoliters to about 20 nanoliters, even more often in the range of about 1 nanoliter to about 20 nanoliters, and most often in the range of about 5 nanoliters to about 15 nanoliters. The reagents may include a labeled nucleic acid probe, PCR primers (e.g., forward primers and reverse primers), a thermostable DNA polymerase, an aqueous buffer, magnesium chloride and deoxynucleotide triphosphates, and may also include other non-reactive ingredients.

In an alternate embodiment, the sample may be pre-amplified prior to pooling with the forward primers. In the preliminary amplification reaction, the reverse transcribed sample is mixed with all forward and reverse primers and then subjected to about 10 cycles to about 18 cycles of PCR. Using 14 PCR cycles, the pre-amplification reaction increases the nucleic acid analytes by about 16,000 fold. The pre-amplification reaction is described in more detail in Specific Example 1, below.

Querying for the Target Sequence of Interest

In step 108, the experiment is run. For example, a homogenous assay may be performed such as real time PCR. In this assay, the labeled nucleic acid probe contains a stretch of nucleic acid sequences that are capable of recognizing 8-mer and 9-mer motifs in the target nucleic acid analyte, as described above. FRET quenching of the labeled nucleic acid probe is irrevocably eliminated when the Taq polymerase reaches the region where the labeled probe is annealed to the target nucleic acid analyte, recognizes the probe-template hybrid as a substrate, and subsequently hydrolyzes phosphodiester bonds of the probe during primer-directed DNA amplification. The hydrolysis reaction irrevocably releases the quenching effect of the quencher dye on the reporter dye, thus resulting in increasing detector fluorescence with each successive PCR cycle.

The homogenous assay of the invention should not be construed to be limited to PCR-based detection methods, but may employ any method of detection and/or quantification to detect and/or quantify a target nucleic acid analyte. In one aspect, PCR may be used to amplify a target. In another aspect, other amplification systems or detection systems may be used, including systems described in U.S. Pat. No. 7,118,910, which is incorporated herein by reference in its entirety. In a further aspect, a detection system other than PCR may be used such as an Invader® assay (Third Wave, Madison, Wis.). In one aspect, real time quantification methods may be used to determine the quantity of a target nucleic acid analyte present in a sample by measuring the amount of amplification product formed during or after the amplification process itself. Fluorogenic nuclease assays are one specific example of a real time quantification method that may be used successfully with the matrix-type microfluidic devices described herein. This method of monitoring the formation of amplification product involves the continuous measurement of PCR product accumulation using a dual-labeled nucleic acid probe, such as a hydrolysis probe. It will be appreciated that the invention is not limited to use of these probes and any tag-specific probe may be used.

In an embodiment according to the invention, the aliquots in the reaction chambers may be queried for the presence of the targeted nucleic acid analyte, which is accomplished by the use of the labeled probes. The fluorescent signal may be monitored and quantified with fluorescence detectors, such as fluorescence spectrophotometers and commercial systems that allow the monitoring of fluorescence in PCR reactions.

Alternatively, however, the probe may be unlabeled, but may be detectable by specific binding with a ligand which is labeled, either directly or indirectly. Suitable labels, and method for labeling probes and ligands are well known in the art, and include, for example, radioactive labels which may be incorporated by known methods (e.g., nick translation, random priming or kinasing), biotin, fluorescent groups, chemiluminescent groups (e.g., dioxetanes) enzymes, antibodies, gold nanoparticles and the like. Variations of this basic scheme are known in the art, and include those variations that facilitate separation of the hybrids to be detected from extraneous materials and/or that amplify the signal from the labeled moiety.

It will be appreciated that specifically at least about 10, more often at least about 25, still more often at least about 50, even more often at least about 100, in some cases at least about 500 and sometimes at least about 1000 targets may be detected using the methodology of the invention. Thus, the method may make use of at least about 10, more often at least about 25, still more often at least about 50, even more often at least about 100, in some cases at least about 500 and sometimes at least about 1000 target-specific probes.

Data Output and Analysis

Figure 6:
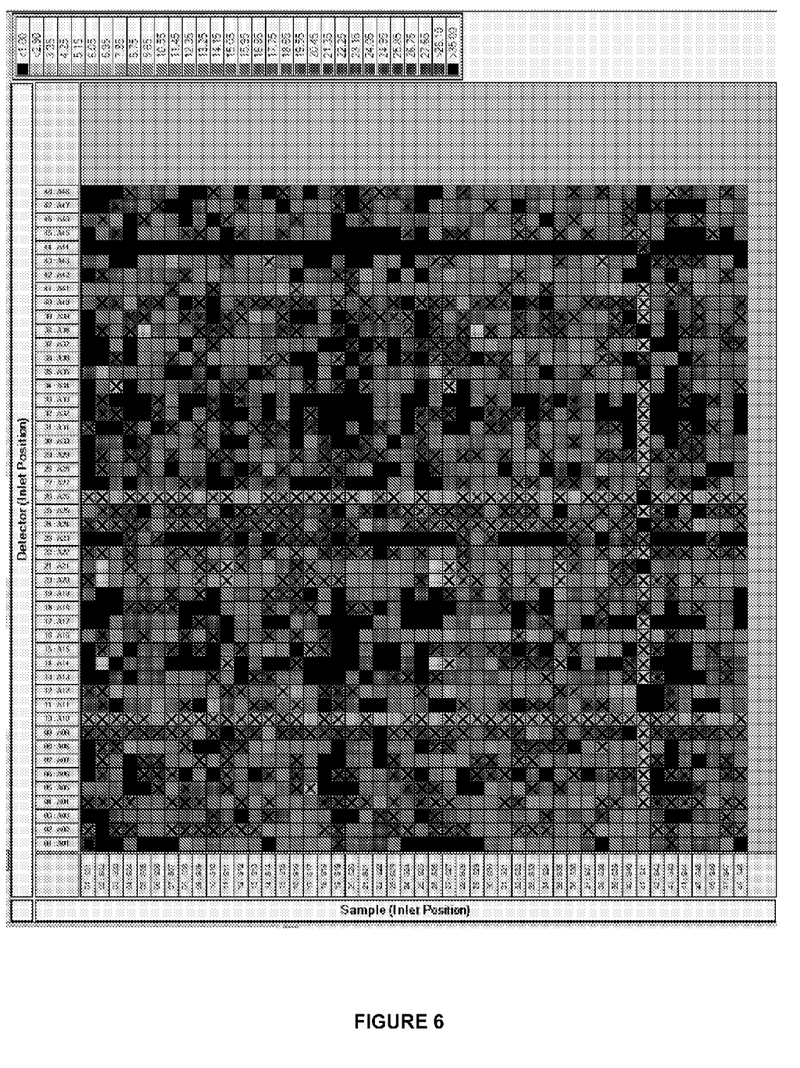
FIG. 6 shows the heat output map for a 24×48 reaction array.

In step 110, the gene expression data is output as a heat matrix, shown for example in FIG. 6, which shows a heat matrix of a 24×48 array. In FIG. 6, each square, representing a reaction chamber on the DA matrix, has been assigned a color value shown in gray scale for the purposes of this application only, however, typically, the data output would be shown in color. The black squares mean no gene expression was detected, the white squares indicated the highest level of gene expression, with the shades of gray indicating levels of gene expression in-between. In a further aspect, a software program may be used to compile the data generated in the heat matrix into a more reader friendly format.

Without further elaboration, it is believed that one skilled in the art using the preceding description can utilize the invention to the fullest extent. The following examples are illustrative only, and not limiting of the disclosure in any way whatsoever.

EXAMPLES

Specific Example 1

Analysis of Nucleic Acids from One Sample Using an 48.48 Dynamic Array

In this example, 64 target nucleic acid analytes were assayed from one sample using a 48.48 Dynamic Array (Fluidigm Corporation, South San Francisco). The 64 target nucleic acid analytes assayed are referred to as Target Nos. 1-64. For each target nucleic acid analyte, a hydrolysis probe was selected from the Roche Universal ProbeLibrary (UPL) (Roche Applied Sciences, Indianapolis, Ind.) and PCR primers (forward and reverse primers) designed to amplify specific target nucleic acid analytes. The assay was carried out in the following manner.

A preliminary amplification reaction was performed to obtain the pre-amplified sample. The preliminary amplification reaction was performed by combining cDNA obtained from a sample with 64 forward primers and 64 reverse primers at 50 nM each and used with AB TaqMan® PreAmp Master mix to amplify the cDNA for 14 cycles. The preliminary amplification reaction resulted in a 16,000 fold amplification of the nucleic acid analytes. The preliminary amplification reaction was performed by combining 6.25 µL Human Universal cDNA (BioChain Institute Inc., Hayward, Calif.), 6.25 µL of a solution containing 128 oligonucleotide primers each at a concentration of 200 nM, and 12.5 µL of 2× TaqMan® PreAmp Master Mix (Applied Biosystems, Foster City, Calif.). This reaction was incubated at 50° C. for 2 min, 95° C. for 10 min, followed by 14 cycles of 15 sec at 95° C. and 4 min at 60° C.

Figure 7:
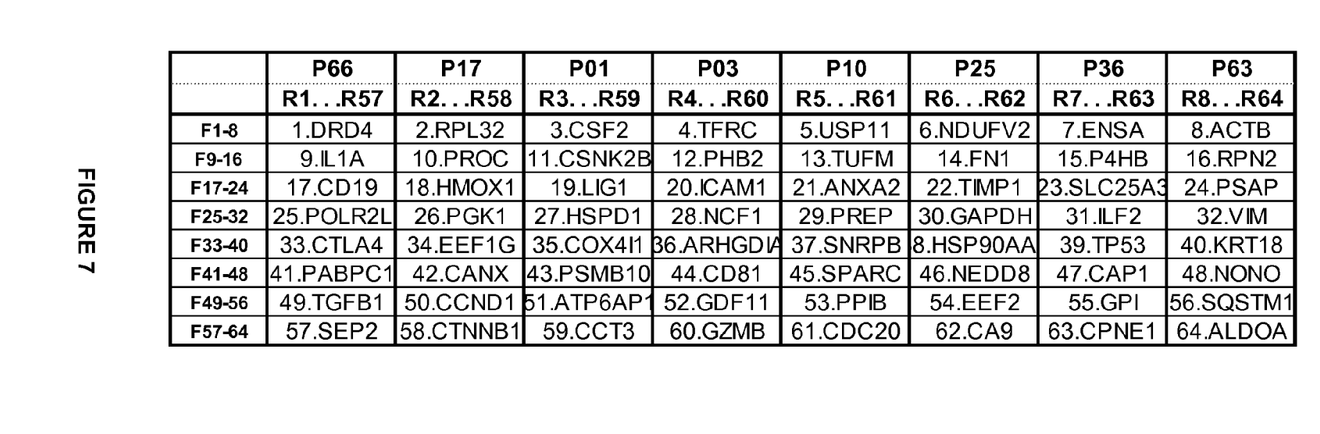
FIG. 7 shows the pooling configuration of the study conducted in Specific Example 1. The forward primers were pooled in groups of 8 and the reverse primers were pooled in groups of 8 as indicated in the matrix.

The forward primers were pooled in groups of 8 and the reverse primers were pooled in groups of 8 as indicated in the matrix of FIG. 7. The reverse primers were combined with the indicated UPL probes and dispensed into the Assay inlets of the 48.48 array (Fluidigm Corporation, South San Francisco). The solutions added to the Assay inlets consisted of the eight reverse primers each at a concentration of 2 µM, the UPL probe at a concentration of 1 µM, and 0.25% Tween 20. The forward primer mixes were combined with different dilutions of the preamplified sample, master mix, and DA sample loading buffer, and dispensed in the Sample Inlets of the 48.48 array. Each solution added to the Sample inlets was prepared by mixing 1 µL of a solution containing 8 forward primers each at a concentration of 2 µM, 2.5 µL of the preamplified sample, 5 µL 2× TaqMan® Universal Master Mix (Applied Biosystems, Foster City, Calif.), and 0.5 µL 20× Sample Loading Buffer (Fluidigm Corporation, South San Francisco). After loading using the NanoFlex™ IFC Controller (Fluidigm Corporation, South San Francisco), PCR and fluorescence detection were performed in the BioMark™ System (Fluidigm Corporation, South San Francisco) for genetic analysis. The thermal cycling protocol consisted of 50° C. for 2 min, 95° C. for 10 min, followed by 40 cycles of 15 sec at 95° C., 5 sec at 70° C., and 1 min at 60° C. The final concentrations in the reaction chambers of the array were 200 nM each forward and reverse primers and 100 nM UPL probe.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology or in the relevant fields are intended to be within the scope of the appended claims.

The disclosures of all references and publications cited above are expressly incorporated by reference in their entireties to the same extent as if each were incorporated by reference individually.

What is claimed is:

1. An assay method comprising:
   providing a device comprising a plurality of chambers arrayed in columns and rows;
   providing a plurality of nucleic acid molecules;
   combining, in individual chambers, a labeled nucleic acid probe, a combination of forward PCR primers, a combination of reverse PCR primers, and at least one nucleic acid molecule, whereupon:
      the chambers in each column contain the same probe;
      the chambers in each column contain the same combination of reverse primers;
      the chambers in each row contain the same combination of forward primers;
      the chambers in at least two columns contain different probes;
      the chambers in at least two columns contain different combinations of reverse primers;
      the chambers in at least two rows contain different combinations of forward primers; and
      at least some chambers contain
         (a) a forward primer and a reverse primer capable of amplifying a region of a nucleic acid molecule of the plurality of nucleic acid molecules, if the nucleic acid molecule is present in the chamber, to produce amplicons, and
         (b) a probe that specifically binds the amplicons produced in (a);
   exposing the chambers to conditions that promote production of amplicons; and
   querying each chamber for the production of amplicons.

2. The method of claim 1, further comprising performing a preliminary amplification reaction on the plurality of nucleic acid molecules prior to said combining step.

3. The method of claim 2, wherein the preliminary amplification reaction comprises making a reaction mix containing the plurality of nucleic acid molecules, forward PCR primers, and reverse PCR primers and subjecting the reaction mix to PCR amplification.

4. The method of claim 3, wherein the reaction mix is subjected to from about 10 cycles to about 18 cycles of PCR amplification.

5. The method of claim 4, wherein the reaction mix is subjected to about 14 cycles of PCR amplification.

6. The method of claim 1, wherein the plurality of nucleic acid molecules comprises cDNA molecules.

7. The method of claim 1, wherein the conditions promote hybridization of the probes to the amplicons.

8. The method of claim 1, wherein said exposing comprises performing PCR.

9. The method of claim 8, wherein the PCR is real time PCR.

10. The method of claim 1, wherein the probes are capable of detecting about 8-mer or about 9-mer motifs on amplicons.

11. The method of claim 1 wherein at least one probe in said combining step is labeled on a 5' end with a fluorescent molecule and labeled on a 3' end with a dark quencher dye.

12. The method of claim 1, wherein the device comprises a 48×48 array of chambers.

13. The method of claim 1, wherein the device comprises a 96×96 array of chambers.

14. The method of claim 1, wherein at least 1000 different amplicons are detected.

15. The method of claim 1, wherein only one distinct amplicon is generated in each chamber.

16. The method of claim 1, wherein, in at least one column, the probe specifically binds the amplicons produced in at least two chambers of the column, wherein the probe binds first amplicons in one of the at least two chambers and binds second amplicons in another of the at least two chambers, and said first amplicons and second amplicons are not the same.

* * * * *